United States Patent [19]

Olsson et al.

[11] Patent Number: 5,265,594
[45] Date of Patent: Nov. 30, 1993

[54] APPARATUS FOR REGULATING THE FLOW-THROUGH AMOUNT OF A FLOWING MEDIUM

[75] Inventors: Sven-Gunnar Olsson, Arloev; Goeran Skog, Bromma; Bo Dahlstroem, Vaellingby; Dan Linden, Stockholm; Goeran Cewers, Lund; Mats Iderup, Malmoe; Goeran Rydgren, Bunkeflostrand, all of Sweden

[73] Assignee: Siemens Aktiengesellschaft, Munich, Fed. Rep. of Germany

[21] Appl. No.: 784,761

[22] Filed: Oct. 30, 1991

[30] Foreign Application Priority Data

Oct. 30, 1990 [EP] European Pat. Off. ........ 90120843.9

[51] Int. Cl.$^5$ ............................................ A61M 16/00
[52] U.S. Cl. .......................... 138/204.18; 128/204.21; 128/204.23; 128/205.24
[58] Field of Search ...................... 128/204.18, 204.21, 128/204.23, 205.24

[56] References Cited

U.S. PATENT DOCUMENTS 3,741,208  6/1973  Jonsson et al. ................. 128/204.21
3,972,327  8/1976  Ernst et al. ...................... 128/204.23
4,463,332  7/1984  Everett .............................. 335/258

FOREIGN PATENT DOCUMENTS 430837  8/1967  Switzerland .
2026326  2/1980  United Kingdom .

OTHER PUBLICATIONS

Puritan-Bennett 7200 Microprocessor Ventilator Advertising Brochure.
"Some Aspects of the Dynamic Behaviour of Aircrew Breathing Equipment," Allen et al. Aerospace Medicine, vol. 36, No. 11, Nov. 1965.
"A Servo-Controlled Breathing Simulator," Maslen, Royal Aircraft Establishment Technical Report 68213 Aug., 1968.

Primary Examiner—Edgar S. Burr
Assistant Examiner—Aaron J. Lewis
Attorney, Agent, or Firm—Hill, Steadman & Simpson

[57] ABSTRACT

An apparatus, such as a ventilator, for regulating the flow-through amount of a flowing medium, such as a gas, has a valve with a variable orifice operated by a first regulating circuit with negative feedback. The regulating variable generated by the first regulating circuit controls the size of the orifice so that the difference between a desired value and an actual value for the flow-through amount os minimized, toward zero. To achieve rapid changes in the flow-through amount with a high regulating precision, at least one further regulating circuit is provided to which the regulating variable of the first regulating circuit is supplied as the desired value. The actual value for the further regulating circuit may be the measured position of the closure element for the orifice. The bandwidth and the gain can be optimized for each regulating circuit. The energy consumption can be lowered by current recovery and battery operation can be simplified, in the event of a power outage.

28 Claims, 5 Drawing Sheets

APPARATUS FOR REGULATING THE FLOW-THROUGH AMOUNT OF A FLOWING MEDIUM

BACKGROUND OF THE INVENTION

1. Field of the Invention

The present invention is directed to an apparatus for regulating the flow-through amount of a flowing medium, such as a ventilator for regulating the flow-through amount of a gas.

2. Description of the Prior Art

Ventilator arrangements are known in the art such as disclosed, for example, in U.S. Pat. No. 3,741,208. Ventilators of this type control the gas flow to or from a patient using an analog electronic circuit with negative feedback. An adjustable reference value for the chronological curve of the desired gas flow is generated by a rated value generator. A gas flow meter defines the actual value for the current gas flow, and converts this value into a corresponding electrical signal which, after linearization, is supplied to the input of a difference-forming stage. The reference value is supplied to the other input of the difference-forming stage by the rated value generator. The output signal of the difference-forming stage forms the proportional part of the regulating variable, which serves the purpose of driving a stepping motor. The stepping motor moves a closure element disposed in a gas conduit, by which the cross section of the internal opening of the conduit can be varied, so that the difference between the current gas flow and the desired gas flow is maintained as close to zero as possible. An integral component combined with the proportional component of the regulating variable in a known manner.

The ventilator disclosed in U.S. Pat. No. 3,741,208 was the first to successfully achieve various time-dependent respiration patterns in a reproducible manner.

Another ventilator is described in the brochure (Form AA-213, May, 1983) for the PB 7200 Microprocessor Ventilator of the Puritan-Bennett Corporation. In this ventilator, a digital regulation takes place wherein the current gas flow is measured in analog fashion using a hot-film manometer, and the analog value is digitized and intermediately stored for subsequent use in a microprocessor for calculating a regulating variable together with a value from a table for the desired gas flow, which is also stored and is used as the rated value. The regulating variable thus consists of a proportional component, a differential component, and an integral component to which a constant is added for the purpose of preventing seizing of the closure means at the valve opening. A solenoid value as disclosed, for example, in U.S. Pat. No. 4,463,332 is used as the valve. An oblong magnetic element is provided as the closure element, which is pressed against the valve opening by means of a resilient membrane, which exerts a linear spring force on the magnetic element. When a current is applied to the coil of the solenoid valve, a force opposite the spring force is generated as a function of the magnetic flux, which lifts the magnetic element from the valve opening to adjust the opening in accordance with the equilibrium position which is achieved. The structure of the valve is selected so that movement of the magnetic element is linearly proportional to the applied electrical current.

A single control circuit having negative feedback is provided in each of the above known ventilators for controlling the position of the closure element or closure means in order to regulate the gas flow.

An article entitled "Some Aspects of The Dynamic Behavior of Air Crew Breathing Equipment" appearing in Aerospace Medicine, Vol. 36, No. 11, November, 1965 describes a respiration simulator wherein the desired gas flow is not controlled via a value, but by means of a piston motion, with some degree of regulation being indicated. The gas flow, the position of the piston, and the speed of the motor with which the piston is driven are defined as the actual quantities. All three actual values, are compared to a single rated value, which is a reference signal generated by a so-called "wave-form generator" for the chronological curve of the desired gas flow. This takes place in a single control circuit, i.e., the electrical signals received corresponding to the various actual values are substracted in common from the reference signal. A faultless regulation is thus not possible under normal conditions, because the different actual values disturb each other. For example, the actual value for the gas flow may be above the rated value and have the effect of reducing the current flow, whereas the actual value for the position of the piston, by contrast, may indicate an excessively low gas flow and act in the opposite direction, i.e. toward an increase in the gas flow.

SUMMARY OF THE INVENTION

It is an object of the present invention to provide a regulator for the flow-through amount of a flowing medium wherein the desired value for the flow-through amount is quickly achieved with high regulating precision.

It is a further object of the present invention to provide such an apparatus wherein a regulating time shorter than 10 milliseconds is achievable.

Another object of the present invention is to provide such an apparatus wherein the necessary electrical power for operating the apparatus is as low as possible.

Another object of the present invention is to provide such an apparatus which operates faultlessly within a large pressure range of the medium which is supplied to the regulating valve in the apparatus.

It is a further object of the invention to provide such an apparatus wherein the regulating valve is closeable reliably and quickly given an outage of the regulating variable in order to prevent uncontrolled output of the flowing medium.

It is an object of the present invention to provide a ventilator to regulating the flow of respiratory or anesthetic gas which has the above features.

The above objects are achieved in an apparatus constructed in accordance with the principles of the present invention having a valve through which the medium to be regulated flows, the valve having an opening or orifice which is adjustable in cross section by a movable closure element. Means are provided for mechanically controlling the position of the closure element. Means are provided for calculating an actual value of the flow-through amount, the actual value being supplied to a first regulating circuit which generates a first regulating variable, using negative feedback, for controlling the position of the closure element. The first regulating circuit is also supplied with a rated value, corresponding to a desired flow-through amount, generated by a rated value generator. The first regulating circuit controls the position of the closure element so that the difference between the rated value and the actual value of the flow-through amount is maintained as close to zero as possible. The apparatus also includes means for calculating an actual value corresponding to the position of the closure element, and a second regulating circuit to which this further actual value is supplied. The first regulating variable from the first regulating circuit is supplied as a rated value to the second regulating circuit, which generates a second regulating variable, also using negative feedback, from the difference between the rated value and the actual value for the position of the closure element. The second regulating variable is supplied to the means for controlling the position of the closure element so that the difference between the rated value and the actual value of the position of the closure element is as close to zero as possible.

DESCRIPTION OF THE PREFERRED EMBODIMENTS

Figure 1:
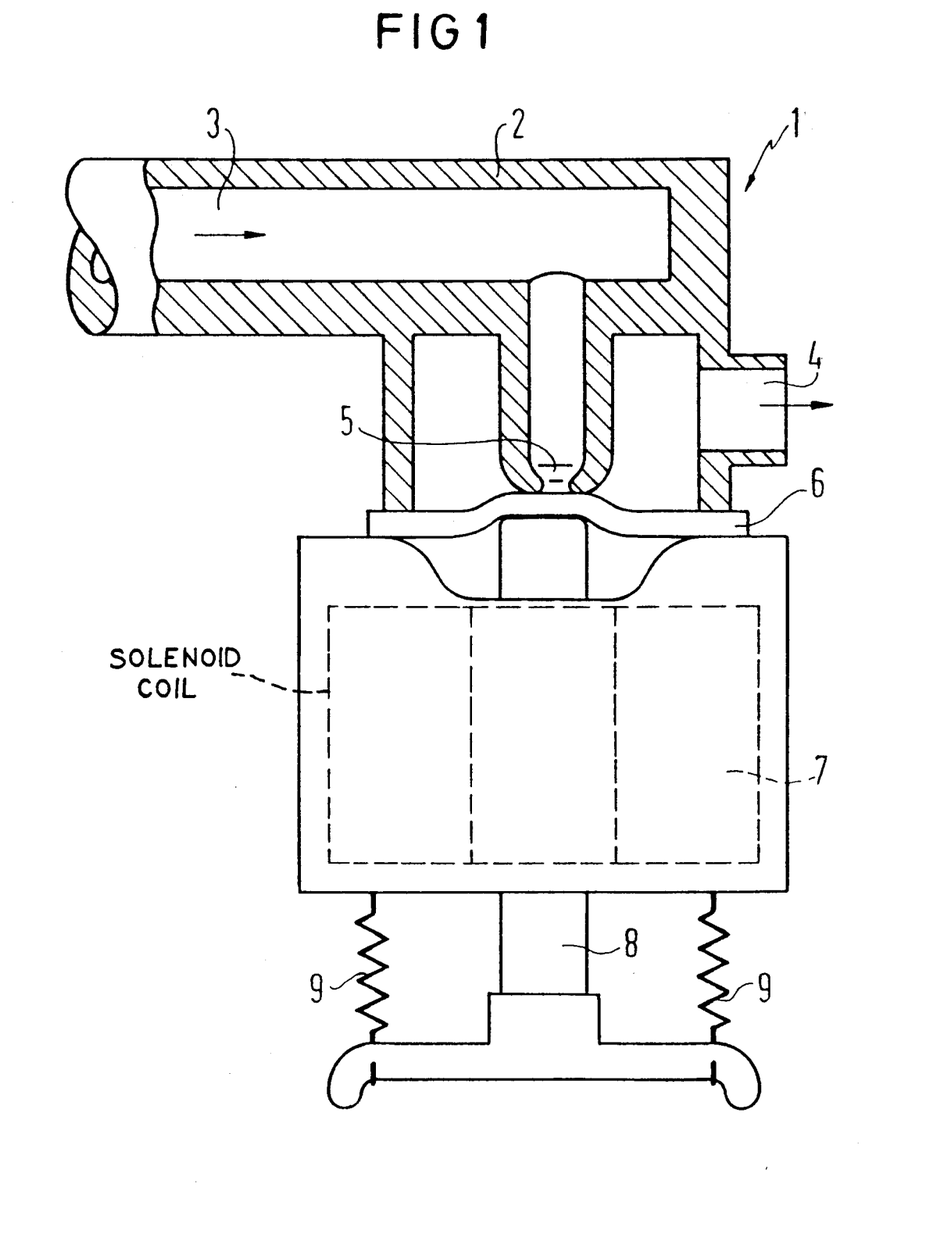
FIG. 1 is a side view, partly in section, of a solenoid valve for use in an apparatus constructed in accordance with the principles of the present invention.

A solenoid valve 1, suitable for use in an apparatus constructed in accordance with the principles of the present invention, is shown in FIG. 1. The solenoid valve 1 includes a housing 2 containing a channel for a fluid, such as a gas, to be regulated. The channel within the valve 1 is divided into an inlet 3 and an outlet 4, with a valve opening or orifice 5 disposed therebetween. A membrane 6, consisting of a suitable type of rubber or similar material, is seated so as to normally close the valve opening 5. An encapsulated magnetic coil 7 is disposed below the membrane 6. A rod 8 consisting of, for example, stainless steel clad with magnetic material in the region of the coil 7, is mounted so as to be centrally displaceable within the magnetic coil 7. When there is no current flowing through the magnetic coil 7, the rod 8 is pressed against the membrane 6 by tension springs 9, so that the valve opening is reliably closed. It is also possible to bias the rod 8 using compression springs. In both instances, a desired safety feature is achieved, in that the solenoid valve 1 will automatically close in the event of a power outage, so that an uncontrolled output of a respiratory gas, for example, to a patient, is prevented.

When the magnetic coil 7 is energized by a current, the rod 8 is drawn into the coil, and the membrane 6 is correspondingly lifts away from the valve opening 5 due to its own spring force, and due to the gas pressure at the inlet 3.

Given hypercritical pressure conditions (a large difference between the pressure at the inlet and outlet sides), at a valve opening, the gas flow is proportional to the cross-sectional area of the opening as well as to the quotient of the absolute pressure at the inlet and the absolute pressure at the outlet. By varying the distance of the membrane 6 from the valve opening 5 in the valve of FIG. 1 by adjusting the current through the coil 7, the effective cross-sectional area of the opening 5 is varied, and thus the gas flow is also varied. The force exerted by the flux generated by the magnetic coil 7 on the rod 8 is approximately proportional to the current flowing through the coil 7. The effects of magnetic hysteresis and non-linearities can be substantially avoided by selecting a proper operating point.

Friction in the bearings (not separately shown) which guide the rod 8 and magnetic hysteresis will, however, result in the current needed to open the valve 1 to a specific position being different from the current needed to close the valve 1 to the same position. Given extremely small gas flows, the position is no longer linear relative to the current, because the membrane 6 functions as an additional spring.

Figure 2:
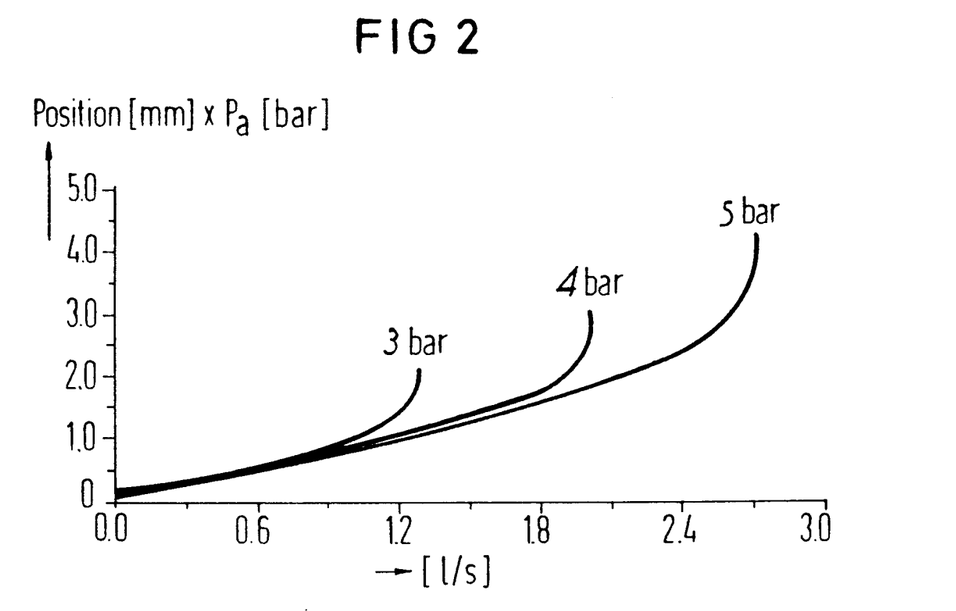
FIG. 2 is a graph showing the dependency of the gas flow on the position of the closure element in the valve of FIG. 1.

The diagram shown in FIG. 2 illustrates the dependency of the gas flow on the position of the rod 8, multiplied by the absolute gas pressure at the inlet side, for three different absolute pressures, i.e., three bar, four bar and five bar. As can be seen in FIG. 2, the gas flow is approximately proportional to the position of the rod 8 over broad ranges for a given pressure.

A ventilator having only one control circuit for the gas flow, with the regulated quantity generated by circuit being directly used to control the current applied to the magnetic coil 7, requires a number of properties in order to function. The aforementioned hysteresis effects must be compensated, but the available amplification of the control circuit is not sufficient for this purpose. Moreover, in order to make the valve operate somewhat rapidly, the amplification must be significantly changed with the gas flow. The amplification must be exactly set for each desired gas flow, otherwise the control circuit will begin to resonate.

Given these practical limitations, only a limited speed with which the position of the valve can be set can be achieved. In a control circuit which only takes the gas flow into consideration, the main problem is that the resonateable gas column will have the tendency to overshoot the desired position given too large a controlled gain. Tests have shown that setting times have been achieved in the range of approximately 20 milliseconds.

Figure 3:
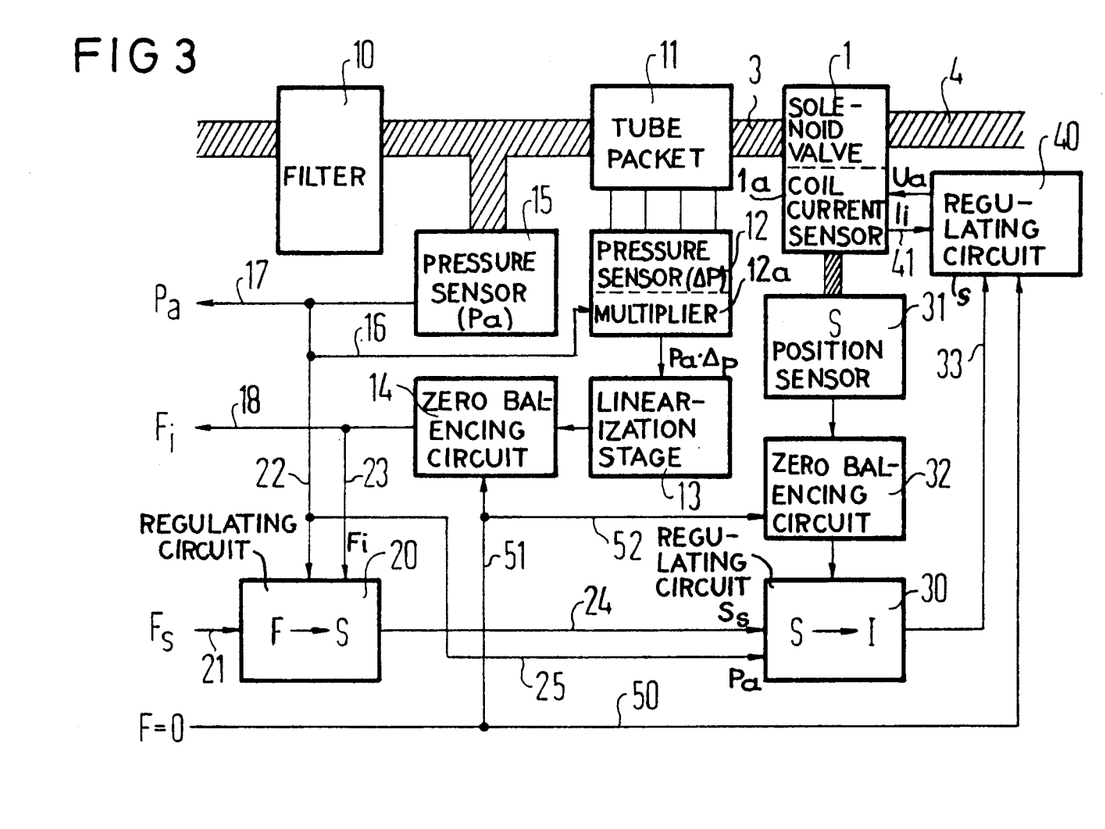
FIG. 3 is a block diagram of a first embodiment of a ventilator constructed in accordance with the principles of the present invention.

As a result of these limitations, a different regulating strategy is used in the apparatus disclosed herein, which is set forth in a first embodiment in FIG. 3.

In FIG. 3, the solenoid valve 1 is schematically shown as a block, with the inlet 3 and the outlet 4 being separately shown. A gas, such as a respiratory gas, is conducted to the inlet 3 from a gas source (not shown) via a filter 10, and via a means for calculating the actual value of the flow-through amount, referred to below as a gas flowmeter. In a known manner, the gas flowmeter may consist of a packet 11 of small tubes wherein a defined pressure drop $\Delta p$ arises, and a pressure sensor 12. The pressure drop $\Delta p$ is calculated from the difference between the respective pressures at the input and output sides of the packet 11. The current gas flow, i.e., the actual value $F_i$, can then be calculated as the product of $\Delta p$ and $P_a$, with $P_a$ being the gas pressure at the input side, measured by a gas pressure sensor 15. The foregoing product is formed in a multiplier 12a to which the output of the pressure sensor 12 is directly supplied, as well as the output of the pressure sensor 15.

Instead of the packet 11 of small tubes in the flowmeter, it is also possible to use a fiber net, as is known in the art. The pressure drop occurs over an extremely short distance, which enhances the speed of the gas flowmeter.

As also shown in FIG. 3, an output signal from the pressure sensor 12 is linearized in a linearization stage 13, to which the gas pressure $P_a$ is also supplied via a line 16. The output signal of the linearization stage 13 is supplied to a zero-balancing stage 14, which undertakes zero-balancing of the signal in a known manner. The output of the zero-balancing stage 14 represents the actual value $F_i$ of the current gas flow, and can be supplied to a display (not shown). The gas pressure $P_a$ at the input side can also be supplied, via a line 17 to a display (not shown).

FIG. 3 also includes a first control circuit, which generates a regulating signal S using the above input quantities. The regulating signal S causes the difference between the rated value and the actual value for the flow to be driven toward zero. The regulating signal S is supplied via a line 24 to a second regulating circuit 30, wherein it is used as a rated value $S_s$ for the position of the closure element in the solenoid valve 1, i.e., the position of the rod 8 in the embodiment of FIG. 1. The pressure $P_a$ is supplied to the second regulating circuit 30 via a line 25. A means for calculating the position of the closure element, referred to in brief as a position sensor 31, calculates the current position of the rod 8. The output of the position sensor 31 is supplied to a zero-balancing stage 32, and the output of the zero-balancing stage 32 is supplied to the second regulating circuit 30 as an actual value $S_i$ for the position of the rod 8. The second regulating circuit 30 calculates a regulating variable I from its input values, which is supplied as a rated value $I_s$ to a further regulating circuit 40 via a line 33, the circuit 40 regulating the current in the coil 7. Because the gas pressure $P_a$ at the input side exerts a force on the membrane 6 in a direction causing the valve 1 to open, the current through the magnetic coil 7, thus the rated value $I_s$, should be variable dependent on this gas pressure $P_a$.

Figure 5:
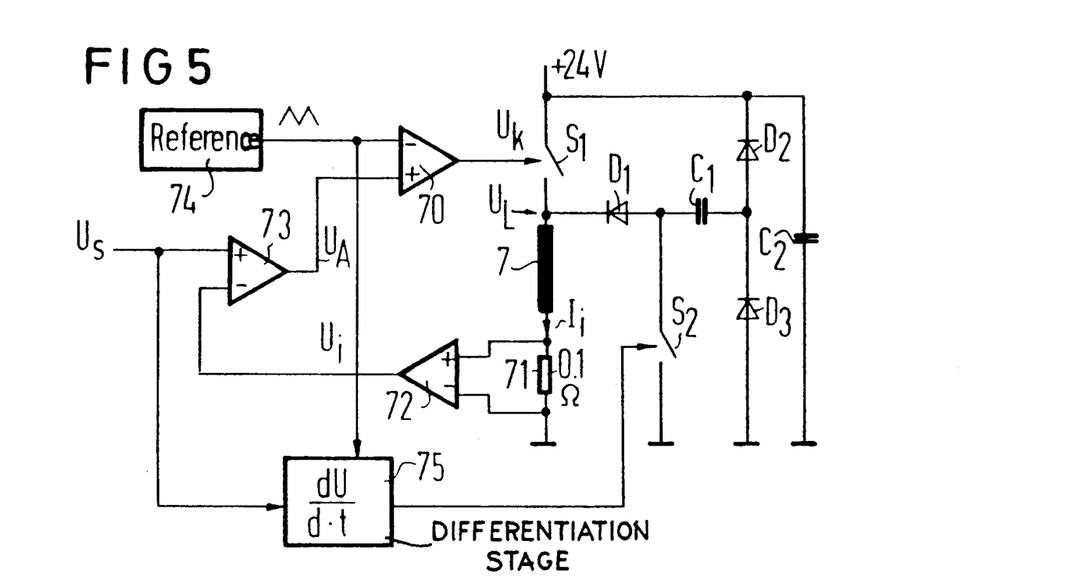
FIG. 5 is a circuit for a pulse width-modulated drive for the solenoid valve shown in FIG. 1 in an apparatus constructed in accordance with the principles of the present invention.

As also shown in FIG. 3, the solenoid valve 1 includes a circuit 1a for calculating the actual value of the current $I_i$ flowing in the coil 7. This actual value $I_i$ is supplied to the regulating circuit 40 via a line 41. From the difference between the actual value $I_i$ and the rated value $I_s$, the regulating circuit 40 calculates a regulating variable $U_a$ which, as discussed in greater detail below with reference to FIG. 5, is employed for a pulse width-modulated control of the current for the solenoid valve 1.

The system of FIG. 3 also includes a line 50 connected to a signal source (not shown) which generates a signal corresponding to a zero gas flow. This signal is supplied to the regulating circuit 40 via line 50, and is also supplied to the zero-balancing stages 14 and 32 via respective lines 51 and 52. The regulating system shown in FIG. 3, wherein three regulating circuits are connected in series in the manner shown, offers a number of advantages. The gain and the bandwidth of each regulating circuit can be individually set at respectively optimum values. All possibilities of high gain and large bandwidth can be used, resulting in combination in a much faster control than has been heretofore available. For example, the regulating circuit 40 for the coil current may have a high bandwidth when the inductance and the resistance of the coil 7 of the solenoid valve 1 are low.

The regulating circuit 30 for the position of the rod 8 can have a higher gain then would otherwise be possible in a regulating circuit for the gas flow. As can be seen from FIG. 2, the position of the rod 8 is linearly proportional to the flow, which means that the correct position, i.e., the rated value for the regulating circuit 30, can be calculated as $F_s/P_a$. The regulating circuit 20 for the gas flow then serves the purpose of fine adjustment.

Further advantages of the regulating system are that error diagnostics and balancing are more easily facilitated, and the reliability of the system is enhanced. For example, the rated value for the position of the rod 8 can be used in combination with the gas pressure of the input side for monitoring the gas flowmeter.

The function of the ventilator shown as an example in FIG. 3 can be summarized as follows. Four parameters of the valve are measured: The gas pressure $P_a$ at the input side, the pressure drop $\Delta p$ via a defined construction, the position $S_i$ of the closure element, and the current $I_i$ through the solenoid coil. Additionally, the actual value for the flow $F_i$ is calculated from $P_a$ and $\Delta p$.

The solenoid valve is controlled by the signal for the rated value of the gas flow. The first regulating circuit 20 for the gas flow forms the signal $S_s$ from the signals $F_s$, $F_i$ and $P_a$. The second regulating circuit 30 for the position of the closure element forms the signal $I_i$ from the signals $S_s$, $S_i$ and $P_a$. The further regulating circuit 40 for the coil current forms a pulse width-modulated signal from $I_s$ and $I_i$, which is supplied to the coil 7.

The following equations indicate, as an example, how the individual regulating variables can be calculated.

$$S_s = S_{sN} + S_{sP} + S_{si}$$

with $$S_{sN} = \frac{F_s}{P_a} \cdot k_1$$

$$S_{sP} = (F_s - F_l) \cdot k_2$$
$$S_{si} = \int (F_s - F_l) \cdot k_3 \cdot dt$$

and $$I_s = I_{sP} + I_{sD} + I_{sPa} + I_4$$
with
$$I_{sP} = (S_s - S_l) \cdot k_4$$

$$I_{sD} = \frac{d(-S_l)}{dt} \cdot k_5$$

$$I_{sPa} = -P_a \cdot k_6$$
and
$$I_4 = k_7$$
and
$$U_a = (I_s - I_l) \cdot k_8$$

Figure 4:
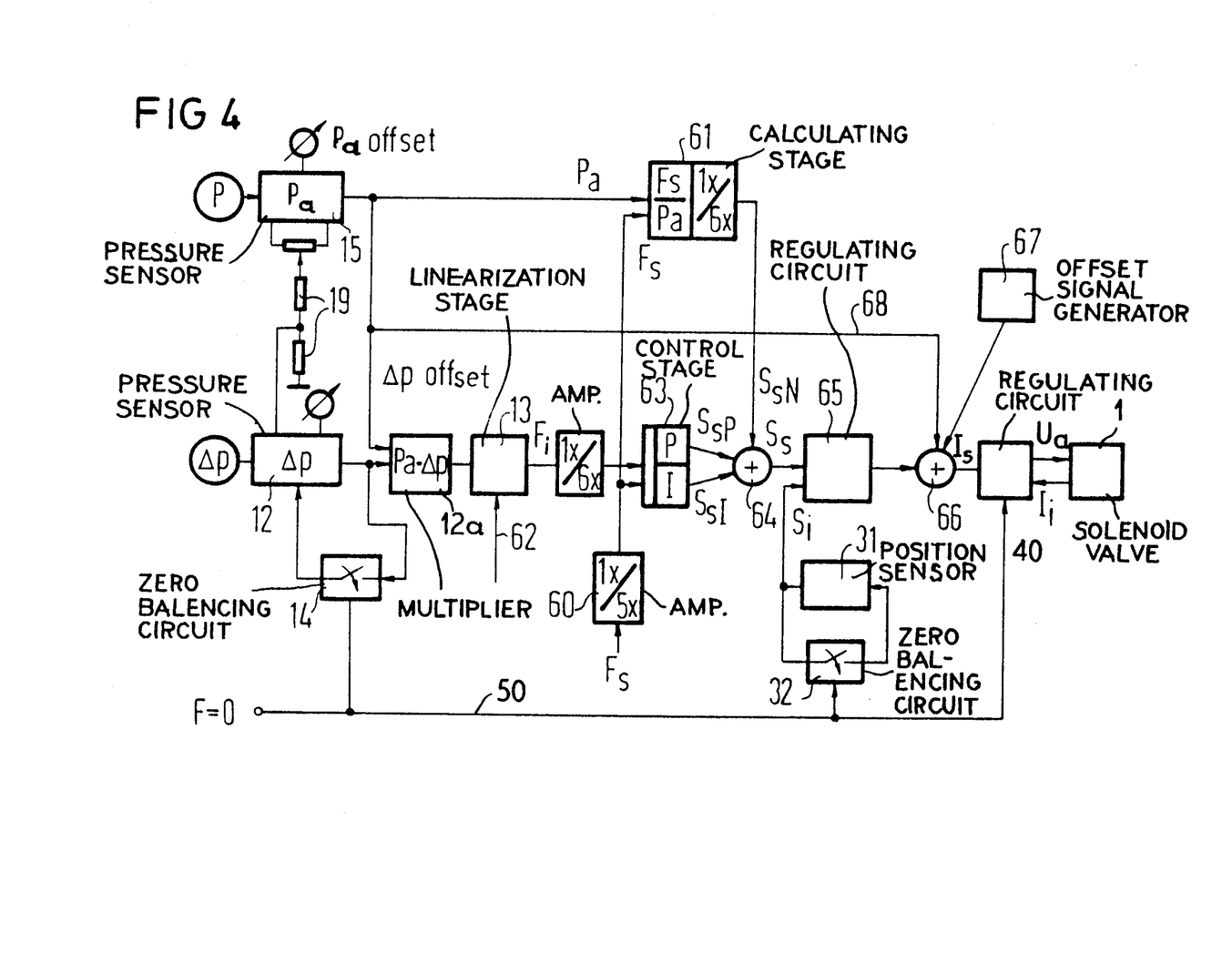
FIG. 4 is a block diagram of a further embodiment of a ventilator constructed in accordance with the principles of the present invention.

A more complete diagram of a ventilator constructed in accordance with the principles of the present invention is shown in FIG. 4, wherein signals and blocks previously identified in connection with FIG. 3 are provided with the same reference symbols. As can be seen in FIG. 4, the gain for the rated value $F_s$ of the gas flow can be varied by an amplification stage 60, or can be attenuated in that stage. The rated value $S_{sN}$ is calculated from the rated value $F_s$ and the pressure $P_a$ at the input side of a calculating stage 61, which may also include an amplification stage for varying the amplification factor applied to the output signal $S_s$ of the calculating stage 61.

In the exemplary embodiment of FIG. 4, the zero-balancing in the zero-balancing stage 14 is already undertaken before the signal is multiplied in the multiplier 12a. This modification of the zero-balancing has no influence on the function.

As already described, the actual value $F_i$ for the gas flow is also calculated. As schematically indicated by an arrow 62 at the linearization stage 13, this can be varied for different gas mixes. The pressure sensors 12 and 15 are each provided with an element for setting a pressure offset. Additionally, a signal corresponding to the gas pressure $P_a$ is supplied via a voltage divider 19 to the pressure sensor 12, and the differential pressure $\Delta p$ is corrected dependent thereon (common mode compensation).

In a control stage 63, forming a part of the first regulating circuit described in connection with FIG. 3, the proportional part and the integral part of the regulating variable are calculated from the rated value and from the actual value of the gas flow. The gain for the integral part of the regulating variable $S_{sI}$ can thus be considerably increased for low gas flows. The proportional part $S_{sP}$ and the integral $S_{sI}$ are added to the rated value $S_{sN}$ in an adder 64. The sum of these signals is supplied at the output of the adder 64 as the rated value $S_s$ to the second regulating circuit 65. This rated value $S_s$ is thus essentially composed of the calculated position value $S_{sN}$ and the regulating variables obtained via the flow control, and serves the purpose of fine adjustment. As can be seen from FIG. 2, the calculated position value $S_{sN}$ becomes imprecise only at extremely low gas flows. The first regulating circuit, including the control stage 63, also contains an offset voltage for the gas flow, which is used for balancing when the rated flow and the actual flow are zero. The actual value for the position $S_i$ is also supplied to the second regulating circuit 65. The output of the regulating circuit 65 is supplied to another adder 66 which also receives an input signal in line 68 from the pressure sensor 15, corresponding to the gas pressure at the input side, and an input from an offset signal generator 67 corresponding to a gas flow of zero. These signals are thus superimposed on the output signal from the second regulating circuit 65, corresponding to the difference between the rated and actual values, so that the force exerted by the gas pressure at the input side is compensated.

The rated value $I_s$ for the current regulation, calculated in this manner, is supplied to the further regulating circuit 40. As described in connection with FIG. 3, the actual value $I_i$ is also supplied to the regulating circuit 40 from the solenoid valve 1, and a signal corresponding to a gas flow of zero is supplied thereto via the line 50.

Circuitry for the pulse width-modulated current control of the solenoid valve 1 is shown in FIG. 5, with only the magnetic coil 7 of the solenoid valve 1 being shown in FIG. 5. In the exemplary embodiment of FIG. 5, a voltage of $+24$ V is applied to the coil 7 via a switch $S_1$. A voltage $U_i$ is obtained at the output of an amplifier 72 having inputs connected in series with the coil 7. The voltage $U_i$ is a measure for the current $I_i$ flowing through the coil 7. A voltage difference ($U_s - U_i$) is amplified in an amplifier 73, the voltage $U_s$ being proportional to the rated value $I_s$. The difference (error) is amplified and, as a voltage $U_a$, is compared in a comparator 70 to a sawtooth voltage generated by a reference voltage generator 74. The output signal of the comparator 70 thus consists of pulses having a pulse duration which increases with increasing error. This, however, is valid only as long as the rated value of the current is higher than the actual value. The circuit also includes a further switch $S_2$, which was assumed to be closed in the above discussion, as a result of which the current through the coil 7 is maintained when the switch $S_1$ is opened. In order to maintain the current through the coil constant, the energy consumed in the resistor 71 and in a diode $D_1$ must be replaced. To rapidly lower the current through the coil 7, the switch $S_2$ is opened. To that end, a differentiation stage 75 calculates the first derivative of the rated value of the current and actuates the switch $S_2$ in the event of an upward transgression of this derivative above a prescribed value. Given an open switch $S_2$, the diode $D_1$, and a further diode $D_3$, are forward conducting, and the magnetic energy in the coil 7, except for the minor losses, is transmitted to a capacitor $C_1$. The voltage across the coil thus becomes approximately $-24$ V (plus the sum of the respective voltage drops across the diodes $D_1$ and $D_3$). The energy of the capacitor $C_1$ is periodically transferred to a capacitor $C_2$, for example at 30 kHz, by briefly synchronously closing the two switches $S_1$ and $S_2$. It is possible in this manner to rapidly increase or lower the current through the coil 7 with low energy losses.

The chronological curves for the rated and actual values of the current, the voltage $U_L$ across the coil 7, and for the voltage pulses $U_k$ generated by the comparator 70 are shown in FIGS. 6A through 6D for the circuit of FIG. 5. For example, the curve of FIG. 6A shows a discontinuous change in the rated value for the current at time $t_1$, which is maintained until a time $t_2$. In FIG. 6B it is shown that the voltage pulses supplied by the comparator 70 are initially broad and continually decrease in duration until they form narrow spikes, by means of which only the losses in the coil are compensated.

Tests have shown that variations in current of approximately 0.5 A/ms can be achieved with a supply voltage of $+24$ V and with a magnetic coil 7 having a resistance of $2\Omega$. The valve can thus open from a low to a maximum gas flow in approximately 5 ms, which is a regulating speed not possible with any known system.

Figure 6:
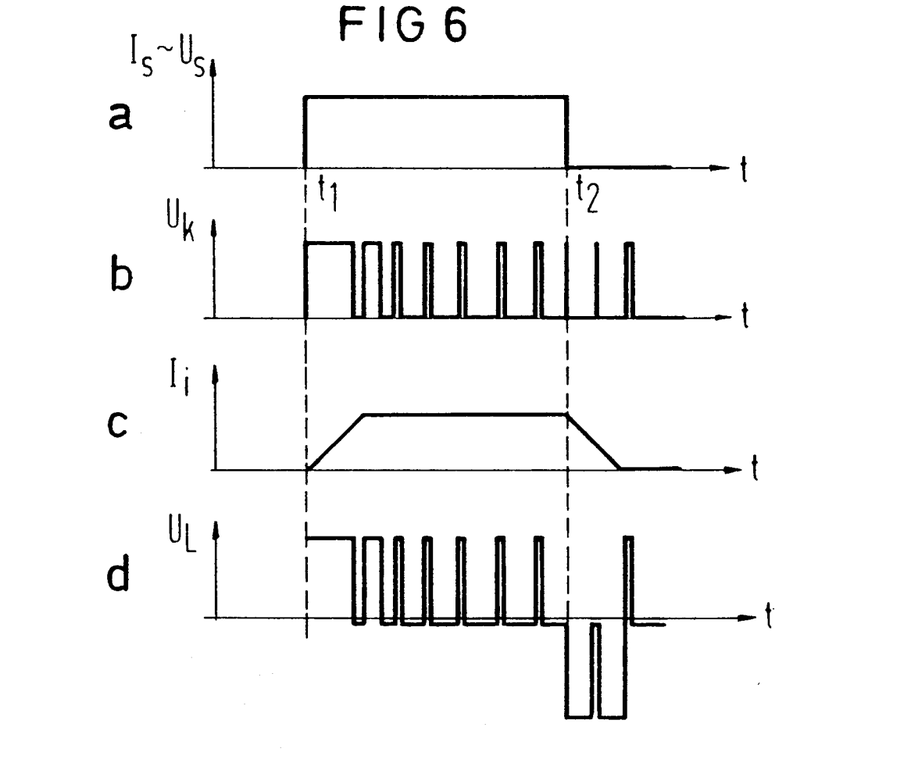
FIG. 6 shows a series of graphs illustrating the chronological curves for the actual and rated values for the circuit of FIG. 5.

In the event that the current through the coil 7 must be very quickly lowered, this can be accomplished using the circuit of FIG. 5 by simply applying $-24$ V to the coil 7, this taking place at the time $t_2$ in the example of FIG. 6, as indicated in the curve shown in FIG. 6d.

In the above exemplary embodiments, analog regulating systems have been described. It is, however, within the scope of the invention disclosed herein to execute the entire regulating system, or at least portions thereof, in digital technology insofar as the components needed for this purpose operate with sufficient speed. It is also possible to digitize the aforementioned four parameters and to control the entire regulation by means of a computer, such as a microprocessor. Thus, for example, the rated value for the position of the closure means can be pre-programmed, so that the closure means, can be brought to the correct position by using the second regulating circuit. The position values for the various gas flows can be stored, for example, in a table.

In all instances, an apparatus, or a ventilator, is obtained which regulates the flow-through amount of a flowing medium extremely quickly with high precision and reliability, both for high and low flow-through amounts. In a ventilator, for example, it is thus possible to control low gas flows for infants as well as high gas flows for adults equally well. The low energy consumption additionally facilitates mobile use of the ventilator, without the necessity of connection to a power line, or if connection to a power line is nonetheless used, the low energy consumption permits back-up operation by means of a battery in the event of a power outage. Moreover, the low-voltage operation also enhances the reliability given the use of a ventilator of this type for anesthesia, because explosive gases are frequently used for that purpose. The high regulating speed also permits high-frequency ventilation to be undertaken with considerably more precision that was heretofore possible.

In the exemplary embodiments described herein, the first regulating circuit was used for controlling the gas flow. It is also within the scope of the invention, however, to precede the first regulating circuit with at least one other regulating circuit in a known manner, for example, by a regulating circuit for the gas pressure with which a patient is to be ventilated. If this is done, the rated value for the gas flow will be practically defined which is necessary in order to maintain the desired gas pressure.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for regulating the flow-through amount of a flowing medium comprising:
   a valve having an input connectable to a source of flowing medium, an output for said flowing medium, a valve opening disposed between said input and said output, and movable closure means for opening and closing said valve by varying the size of said valve opening;
   means for calculating a first actual value, corresponding to the actual flow-through amount of said flowing medium through said valve opening;
   means supplied with a control signal for controlling the position of said closure means in said valve opening dependent on a characteristic of said control signal;
   first regulator means, supplied with a rated value for said flow-through amount and connected to said means for calculating a first actual value to receive said first actual value therefrom, for generating a first regulating variable by negative feedback for use in controlling the position of said closure means so that a difference between said rated value and said first actual value is driven toward zero;
   means for calculating a second actual value, corresponding to the actual position of the said closure means in said opening;
   second regulating means, supplied with said first regulating variable as a rated value and connected to said means for calculating a second actual value to receive said second actual value therefrom, for generating a second regulating variable by negative feedback for use in controlling the position of said closure means so that a difference between said first regulating variable and said second actual value is driven toward zero;
   means for calculating a third actual value, corresponding to an actual value of said control signal characteristic; and
   third regulating means, supplied with said second regulating variable as a rated value and connected to said means for calculating a third actual value to receive said third actual value therefrom and connected to said means for controlling, for generating a third regulating variable forming said control signal for controlling the position of said closure means so that a difference between said second regulating variable and said third actual value is driven toward zero.

2. An apparatus as claimed in claim 1 wherein said valve is a solenoid valve having a coil serving as said means for controlling the position of said closure means based on a control signal supplied to said coil.

3. An apparatus as claimed in claim 2 wherein said control signal characteristic is a current flowing through said coil, and wherein said means for generating a third actual value is a means for generating a third actual value corresponding to the actual current through said coil.

4. An apparatus as claimed in claim 2 wherein said control signal characteristic is a voltage across said coil, and wherein said means for generating a third actual value is a means for generating a third actual value corresponding to the actual value of the voltage across said coil.

5. An apparatus as claimed in claim 2 further comprising:
   means for automatically closing said valve opening in the absence of said control signal for said coil.

6. An apparatus as claimed in claim 2 wherein each of said first, second and third regulating means has a gain and a bandwidth associated therewith, said apparatus further comprising:
   means for varying at least one of the gain or the bandwidth of at least one of said first, second or third regulating means.

7. An apparatus as claimed in claim 2 further comprising:
   means for pulse width-modulating said control signal.

8. An apparatus as claimed in claim 2 further comprising:
   means for recovery of current used to generate said control signal.

9. An apparatus as claimed in claim 2 wherein at least one of said means for calculating a first actual value, said means for calculating a second actual value or said means for calculating a third actual value is an analog circuit.

10. An apparatus as claimed in claim 2 wherein at least one of said first regulating means, said second regulating means or said third regulating means is an analog circuit.

11. An apparatus as claimed in claim 2 wherein at least one of said first regulating means, said second regulating means or said third regulating means is a digital circuit.

12. An apparatus as claimed in claim 11 wherein said at least one of said first regulating means, said second regulating means or said third regulating means which is a digital circuit is a microprocessor.

13. An apparatus as claimed in claim 2 wherein said valve is configured for flow of said flowing medium therethrough so that a pressure of said flowing medium at said input is higher than a pressure of said flowing medium at said output.

14. An apparatus as claimed in claim 1 further comprising:
    means for automatically closing said valve opening in the absence of either said first regulating variable or said second regulating variable.

15. An apparatus as claimed in claim 14 wherein said means for automatically closing said valve opening is a spring-biased means for automatically closing said valve opening.

16. An apparatus as claimed in claim 1 wherein at least one of said means for calculating a first actual value or said means for calculating a second actual value is an analog circuit.

17. An apparatus as claimed in claim 1 wherein at least one of said first regulating means or said second regulating means is an analog circuit.

18. An apparatus as claimed in claim 1 wherein at least one of said first regulating means or said second regulating means is a digital circuit.

19. An apparatus as claimed in claim 18 wherein said at least one of said first regulating means or said second regulating means which is a digital circuit is a microprocessor.

20. An apparatus as claimed in claim 1 wherein said valve has a configuration for said flowing medium so that a pressure of said medium at said input of said valve is higher than a pressure of said medium at said output of said valve.

21. An apparatus as claimed in claim 1 further comprising:
    means for connecting said valve to the respiratory airway of a patient.

22. An apparatus for regulating the flow-through amount of a flowing medium comprising:
    a valve having an input connectable to a source of flowing medium, an output for said flowing medium, a valve opening disposed between said input and said output, movable closure means for closing and opening said valve by varying the size of said valve opening;
    means for controlling the position of said closure means;
    first regulating means for generating a first regulating variable for use in controlling the flow-through amount of said flowing medium through said opening;
    second regulating means for generating a second regulating variable, said second regulating means being connected to said first regulating means for receiving said first regulating variable therefrom for use as a rated value by said second regulating means to form said second regulating variable; and
    third regulating means for generating a third regulating variable, corresponding to a parameter of said closure means, for supply to said means for controlling the position of said closure means, said third regulating means being connected to said second regulating means for receiving said second regulating variable therefrom for use as a rated value by said third regulating means to form said third regulating variable.

23. An apparatus as claimed in claim 22 wherein said parameter is the position of said closure means.

24. An apparatus as claimed in claim 22 wherein said closure means is a voltage-actuated means, and wherein said parameter is the voltage for said voltage-actuated closure means.

25. An apparatus as claimed in claim 22 further comprising:
    means for connecting said valve to the respiratory airway of a patient.

26. An apparatus for regulating the flow-through amount of a flowing medium comprising:
    a valve having an input connectable to a source of flowing medium, an output for said flowing medium, a valve opening disposed between said input and said output, and movable closure means for opening and closing said valve by varying the size of said valve opening;
    means for calculating a first actual value, corresponding to the actual flow-through amount of said flowing medium through said valve opening;
    means for controlling the position of said closure means in said valve opening;
    first regulator means, supplied with a rated value for said flow-through amount and connected to said means for calculating a first actual value to receive said actual value therefrom, for generating a first regulating variable by negative feedback for use in controlling the position of said closure means so that a difference between said rated value and said first actual value is driven toward zero;
    calculating means for calculating a second actual value, corresponding to the actual position of said closure means in said opening;
    means for determining the pressure of said flowing medium and for generating a pressure signal corresponding thereto;
    further calculating means, supplied with said rated value for said flow-through amount and with said pressure signal for calculating a weighted value of said flow-through amount dependent on said pressure;
    summing means for adding said weighted value and said first regulating variable to obtain a sum signal; and
    second regulating means, supplied with said sum signal as a rated value and connected to said means for calculating a second actual value to receive said second actual value therefrom, for generating a second regulating variable by negative feedback for use in controlling the position of said closure means so that a difference between said sum signal and said second actual value is driven toward zero.

27. An apparatus as claimed in claim 26 further comprising:
    means for calculating a third actual value, corresponding to an actual value of said control signal characteristic; and
    third regulating means, supplied with said second regulating variable as a rated value and connected to said means for calculating a third actual value to receive said third actual value therefrom, for generating a third regulating variable for controlling the position of said closure means so that a difference between said second regulating variable and said third actual value is driven toward zero.

28. An apparatus as claimed in claim 26 wherein said further calculating means comprises means for forming a weighted value of said flow-through amount by forming a ratio of said rated value for said flow-through amount and said pressure of said flowing medium.

* * * * *